United States Patent
Peterson

[11] Patent Number: 5,345,828
[45] Date of Patent: Sep. 13, 1994

[54] PROCESS PLANT SAMPLE COLLECTION SYSTEM AND METHOD

[75] Inventor: Roger Peterson, Sweeny, Tex.
[73] Assignee: PMMI, Old Ocean, Tex.
[21] Appl. No.: 882,033
[22] Filed: Jul. 13, 1992
[51] Int. Cl.5 .............................................. G01N 1/20
[52] U.S. Cl. ............................ 73/863.72; 73/863.57
[58] Field of Search ........... 73/863.86, 863.21, 863.23, 73/863.24, 863.25, 863.72, 863.71, 863.73, 863.52, 863.57, 864.33, 863.61

[56] References Cited

U.S. PATENT DOCUMENTS

| | | | |
|---|---|---|---|
| 1,519,827 | 12/1924 | Fuge | 73/863.86 |
| 2,693,114 | 11/1954 | Tapp et al. | 73/863.61 X |
| 2,836,068 | 5/1958 | Clift | 73/863.86 |
| 3,369,405 | 2/1968 | Golagar | 73/863.86 X |
| 3,504,549 | 4/1970 | Davis et al. | 73/863.71 X |
| 3,530,721 | 9/1970 | Hrdina | 73/863.72 X |
| 3,556,730 | 1/1971 | Mitacek | 73/863.86 X |
| 3,827,302 | 8/1974 | Sato | 73/863.72 X |
| 3,950,136 | 4/1976 | Bellinga | 73/863.86 X |
| 4,873,876 | 10/1989 | Sheridan et al. | 73/863.73 X |
| 5,005,432 | 4/1991 | Faulkner | 73/863.86 |

Primary Examiner—Tom Noland
Attorney, Agent, or Firm—Donald Gunn

[57] ABSTRACT

A method and apparatus for obtaining a sample from a on stream plant operation is set forth. In a process plant, with a small pressure differential, fluid flow is provided through an inlet line and surplus is returned through an outlet line connected with the process plant. The inlet and outlet lines connect with a six port, position valve which is switched on rotation. There is a filling position for the valve wherein the filling position enables fluid from the process plant to flow through the inlet line and to fill a buffer tank. Sufficient flow is provided to enable purging of the inlet and outlet lines. Separately, there is a purge gas flow provided for a sample receiving container which is initially purged. On operation of the valve, the intermediate container is forced to flow into the sample receiving container through the valve at the urging the purge gas. A suitable housing is provided with a blanket of nitrogen for safety, and fugitive emissions to atmosphere are prevented. Any discharge from the equipment is through an appropriate filter to prevent atmospheric discharge.

10 Claims, 1 Drawing Sheet

PROCESS PLANT SAMPLE COLLECTION SYSTEM AND METHOD

BACKGROUND OF THE DISCLOSURE

Consider the testing of a chemical processing plant which is placed on line and operates indefinitely. Periodically, it is necessary to test the product made in the plant. That is a difficult task to accomplish in many circumstances, especially those where the process operates at very high pressures and temperatures. Typically, high pressures and temperatures make it difficult to obtain a sample. Moreover, expensive metals and expensive fabrication techniques are required to enable the processing plant to be properly confined within the structure which holds the process. This remains a problem even when only a small sample is required for periodic testing. Not only must the sample be removed from the process plant, the sample must be delivered into a sample container for easy transportation to a lab for testing. Consider as an example a petrochemical processing plant where a process is carried out at elevated temperatures of over 1,000° F. and very high pressures limited primarily by the pressure rating of the equipment of the sample collection system. The fluid flowing in the process pipes and pressure vessels of the processing plant may flow at a rate of hundreds of gallons per minute, and yet only a small portion is required for testing, for example, one liter. There is even the possibility that the sample will change from a gas to liquid on reducing the temperature and pressure to remove the sample. Transfer of the sample from the interior of a process plant through the walls of the pipes or other pressure vessels which contain the process requires tapping the process to obtain the sample, and this must be done without permitting the sample to escape to atmosphere. Except in rare cases, such a sample is at least partially, and often extremely volatile. In any event, a sample must be removed from the processing plant, transferred through a set of flow lines, metered into some sort of sample container, and then delivered for subsequent testing, for instance, at a testing laboratory sample analysis or other testing can be carried out. One mode of testing is to fill a small sample container, carry it to the testing lab, and conduct the test there. This enables a single testing lab to test samples from several different locations on a process plant. For instance, a single process plant may comprise several different columns with intermediate stages of processing, thereby generating samples at 10 or 20 different locations; samples are obtained at different times of the day from the several sample locations, the tests are then run, and product quality and purity is then certified as a result of the laboratory testing.

The present apparatus and method enable periodic testing to be carried out in this fashion. This disclosure sets forth a means and mechanism for such testing notwithstanding the fact that testing is required of the product when the product is manufactured at extremely high pressures and temperatures. Immediately, there is a problem in removal of the sample. For instance, as a result of high process temperatures, the removed product typically will be a gas, and will tend to be reduced in size should it undergo a phase conversion from gas to liquid. On the other hand, because of extremely high pressures, a sample will tend to expand when the pressure confinement is reduced. It is therefore somewhat difficult to scale the amount of sample to be removed so that the proper size and consistent size of sample can be provided in a sample container. The present apparatus enables this to be accomplished. Moreover, it is accomplished in the context where one or several sample containers can be serially filled with each separated from the other at the sample taking stage. The timed separation of samples is accomplished by providing fixed flow lines extending to the sample receiving container which are periodically purged with nitrogen to assure that there is no remnant of sample gas in the lines for later sample collection. The purging of lines assures that two samples taken hours apart are not mixed serially by storage in the connective lines. Moreover, this is all accomplished without permitting fugitive emissions to atmosphere. In part, that is prevented and protected against by utilization of a closed housing which is maintained under a blanket of nitrogen. This assures that there will be minimal accumulation of explosive gases in the housing, or gases which otherwise create some type of hazard. Finally, the system operates so that it can be cyclically controlled by a handle for the purpose of periodic operation of a two position, six port valve.

In summary, the present disclosure is a system for transfer of a sample by means of permanently made connections to a process across a flow restriction in the process. Connection is through an inlet line and outlet line. These connections extend to two ports on a six port valve. There is a sample storage loop in the six port valve. The sample storage loop includes a sized volumetric buffer tank. It is sized so that the sample that is delivered at the prevailing pressure and temperature is held in this buffer tank. To the extent that there is either expansion or contraction by transfer out of the process plant to a reduced pressure and a temperature approaching ambient, there is sufficient size in the buffer tank to permit a properly sized sample to be collected. A purge gas source connected to a needle valve with a flow meter connects to a fifth port, and the sixth valve port is connected by means of a sample line extending to a syringe needle for filling a closed sample container. A sequence of operations is also set forth where the sample is delivered for intermediate holding and later for delivery into the sample receiving container. In addition to that, the equipment operates in a sequence to direct a continuous flow of nitrogen for purging of the connective lines.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
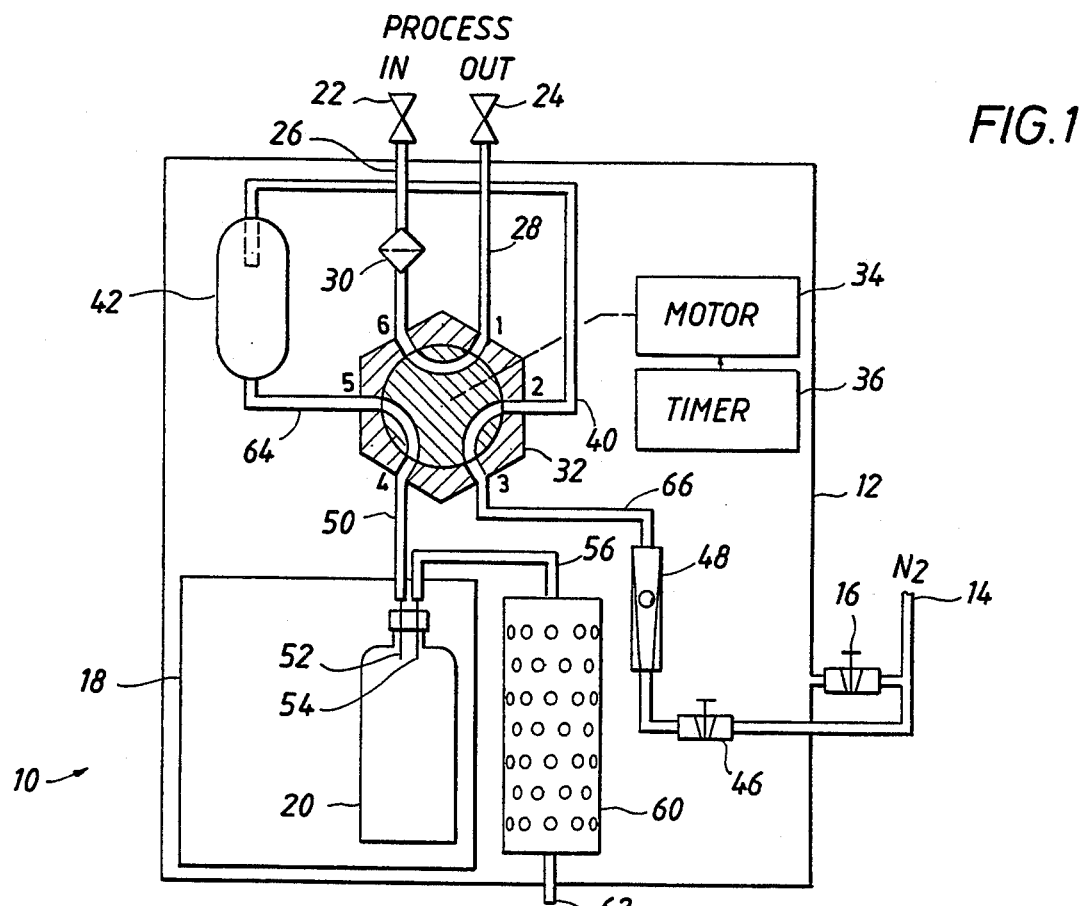
FIG. 1 is a schematic of the sample collecting apparatus of the present disclosure showing a system where the material to be sampled flows through the circulate pathway and is returned by the process and the buffer tank is empty while a nitrogen purge occurs.

In the drawings, the numeral 10 identifies the sample collection apparatus of the present disclosure. This apparatus is constructed within a cabinet 12 which comprises a closed housing. Preferably, it is made of sheet metal, but in many instances, it can be an explosion proof housing or cabinet. To increase and enhance the safety of the system it may be helpful, dependent on the type of material being sampled, to fill this housing with a blanket of nitrogen. A nitrogen source 14 provides a flow of nitrogen through a feed which in turn connects with a needle valve 16, the needle valve being input to the housing 12 to fill the interior with nitrogen. It is desirable to do this in instances where the material being tested tends to form an explosive mixture with air, or perhaps poses some other threat. The remainder of the equipment is preferably located in the housing 12. Conveniently, the housing 12 can be provided with an optional door. The door 18 permits operator handling of the sample receiving container 20 which is installed for holding of a measured sample. Typically, the container 20 is sized to a particular size such as one liter. Typically, it is a closed vessel which is covered over with a cap at the narrow neck or throat of the container. The cap has a hole provided in it large enough to receive the sampling needles and captures a rubber/teflon laminated sheet of material functioning as a septum. The septum is a healing membrane which is punctured but does not leak.

Operation of the system will be described in detail after reviewing the apparatus involved in the present disclosure. To this end, there is a valve 22 which is connected with some aspect of a manufacturing process such as in a distillation column, cat cracker, and the like. The valve 22 is spaced from a similar valve. 24. They are located so that there is some small pressure drop between the two. This enables the inlet line 26 to receive a flow of the process fluid. The inlet line 26 is similar to the outlet line 28 which returns surplus fluid to the process. In a typical circumstance, the pressure in the lines 26 and 28 is substantially the same, and can be easily as high as 500 psi but there is a differential of about 5 or 10 psi. Higher pressures can be handled by heavy duty equipment.

A filter 30 is serially connected in the inlet line 26. In turn, then line 26 also connects with a two position, six port valve 32. The valve has a valve body with a rotor on the interior which is rotated typically by 60° at the urging of a motor 34 connected to the rotor. The motor is periodically operated by a timer 36 to rotate by 60°. This changes the alignment of the ports as will be observed in contrasting FIG. 1 with FIG. 2 of the drawings. Hand operation of the valve is also possible.

The system has other connections to the valve 32. The numeral 40 identifies a line which loops from one port to another port on the valve 32 and serially connects with a buffer tank 42. The tank 42 is an intermediate location which holds the desired quantity of sample. More will be noted regarding the purpose of this intermediate holding step, and especially the amount held at that location.

The nitrogen supply 14 connects through an adjustable needle valve 46 which serially introduces nitrogen flow through a flow meter 48. The flow meter 48 is preferably mounted so that it can be viewed. This assures the operator that nitrogen gas is flowing into the system for purging of the lines as will be described. Another connection to the valve is provided by the sample line 50 which is terminated at a syringe needle 52. That needle introduces sample into the storage container 20. The storage container 20 also provides an outlet for gas in the bottle 20 which is removed through a similar syringe needle 54, flowing in a line 56, and then, in the form of waste products, is delivered through a filter system 60 and vented to atmosphere. The filter 60 is packed with a material which absorbs and purifies the discharge so that the discharged atmosphere is substantially inert, meaning primarily nitrogen gas flow through an atmospheric discharge passage 62. If desired, the outlet 62 can be connected with a flare in the event that the material can be combusted readily.

DETAILED DESCRIPTION OF THE METHOD OF FILLING AND PURGING

Figure 2:
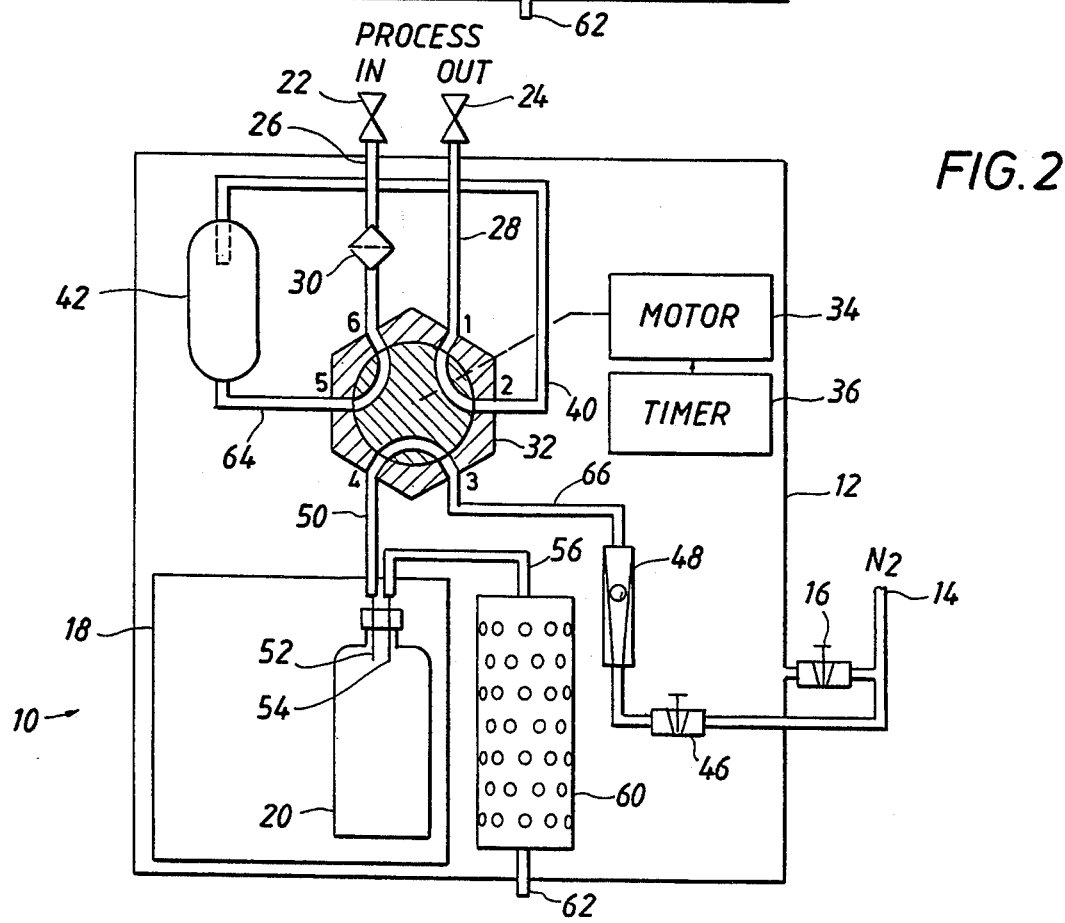
FIG. 2 of the drawings shows the system of FIG. 1 after switching so that connections are altered for filling the buffer tank which is a sequential step in comparison with the arrangement shown in FIG. 1 of the drawings.

Attention is now directed to FIG. 2 of the drawings for a description of a filling and purging sequence. This description will particularly focus on those things which occur when the raw sample is being obtained from the process plant. In FIG. 2 of the drawings, the valve 32 is positioned so that there is a flow path in the following sequence, namely process fluid is delivered through the inlet line 26, flowing into a line 64, the buffer tank 42, the line 40 and back through the valve 32 and to the outlet line 28. As an example, assume that this position of the equipment is maintained for a few minutes so that the process fluid circulates several times through this route. After this, time assures that all the lines and especially the buffer tank 42 are filled with the process fluid, and that is accomplished without dilution. Recalling that the process fluid may be at several hundred psi pressure, and elevated temperature, there is a connection of any needed short or long distance to the present system. Whatever the case, and assuming a requisite interval for circulation in the connected lines just described, the valve 32 is operated from the position shown in FIG. 2 to the position shown in FIG. 1. The first position will be described as the filling position. Filling focuses primarily on filling the container 42. In the filling position shown in FIG. 2, there is sufficient pressure, differential to cause continued flow along the path described. There may however be a phase change dependent on the cooling interval after switching the valve 32 from the position shown in FIG. 2 of the drawings to the position shown in FIG. 1. This movement positions the valve so that there is a completely different arrangement of the connections through the valve and that will be described as the sampling position. The sampling position occurs in the following fashion. The timer 36 in conjunction with the motor 34 moves the valve to 60°. This breaks the connection which was accomplished in the loop 40, and completely reconnects the loop 40. This new flow sequence will then be described beginning with the nitrogen source 14. Nitrogen is delivered ratably through the needle valve 46, through the flow regulator 48, and the line 66. The nitrogen flows through the valve 32 and into the sample loop 40 into the buffer tank 42. Fluid continues to flow through the line 64 back through the valve 32, the line 50 and the syringe 52 for filling the sample receiving container 20. In brief, the nitrogen is delivered at a flow rate and for an interval sufficient to force the atmosphere that was initially in the container 20 out of the container. The container 20 is voided through the filter 60. Moreover, this nitrogen flow path continues to operate so that a sufficient quantity of the sample is forced from the buffer tank 42 along the flow path into the removable sample receiving container 20 to fill it to a desirable level. Vapors contained within container 20 are forced out through the filter but that does not pose a problem with fugitive emissions as a result of the filter operation.

Operator attendance is involved in the present apparatus by removal of a filled sample container 20 and replacement of it with an empty sample container. If a sample is taken every day, then the container 20 is removed daily and replaced. Removal requires pulling the sample container 20 downwardly so that the two syringe needles retract from the septum. This seals the interior. A new sample container is installed by removal of the metal cap over the septum, and pushing the container 20 upwardly so that the two needles are inserted through the septum for filling. This periodic removal and replacement assures that individual samples can be taken at the requisite interval, removed from the area and taken to a test lab, and yet the equipment is left in a condition so that another sample can be collected.

PURGING OF THE LINES

An important feature of this system is the ability to purge the lines continuously. Consider for instance the arrangement of the lines shown in FIG. 2 of the drawings. The nitrogen supply is delivered totally into the sample container 20 and flows out through the filter 60 to atmosphere. This discharges nitrogen to atmosphere, a process which does not deplete the filter 60, but instead protects it from being depleted by absorbing moisture from the atmosphere. Moreover, the line 40 forms a closed loop at this juncture and is able to continuously circulate the process fluid which is to be sampled, and that does not require purging at that moment. When the valve 32 is in the position illustrated in FIG. 1 of the drawings, nitrogen flows along the path previously described to force sample into the container 20. By timed operation of this process taking into account the volumetric capacity of the flow lines and the adjustment of the needle valve 46, the proper amount of nitrogen is transferred and delivered through the system so that the container 20 is properly filled. This repetitive process assures that fugitive emissions to atmosphere do not occur. Overfilling the container 20 poses no problem because the filter prevents atmospheric discharge.

While the foregoing is directed to the preferred embodiment, the scope thereof is determined by the claims which follow:

I claim:
1. An apparatus for sampling a fluid in a process which comprises:
   (a) inlet and outlet lines connected with a process to provide a flow of fluid from the process along the inlet line and returning surplus fluid along the outlet line to the process;
   (b) valve means having ports connected to said inlet line and outlet line;
   (c) a intermediate sample buffer tank having a pair of lines connected thereto which connect with ports of said valve means;
   (d) an additional port to said valve means for providing a purge gas flow into said valve means;
   (e) a sample port on said valve means providing a flow path from said valve means into a removable sample receiving container;
   (f) a flow path from said sample receiving container to vent the sample receiving container of the initial atmosphere therein which might flow through the sample receiving container; and
   (g) wherein said valve means comprises a two position means switchable between a filling position so that said buffer tank is filled, and also having a sampling position wherein said sample receiving container is filled from said buffer tank.
2. The apparatus of claim 1 wherein said inlet and outlet lines connect to a process plant and to ports selectively connected together by said valve means.
3. The apparatus of claim 1 wherein said valve means connects said buffer tank to said inlet line for filling said buffer tank.
4. The apparatus of claim 3 wherein said valve means serially connects said buffer tank with said inlet and outlet lines to enable continued flow therethrough.
5. The apparatus of claim 1 wherein said buffer tank, valve means and said sample storage means are within a closed housing.
6. The apparatus of claim 5 including a purge gas supply means connected to fill said housing with a purge gas.
7. The apparatus of claim 1 including a purge connected serially with said buffer tank.
8. The apparatus of claim 1 including a pair of syringe needles extending into and puncturing a septum of said sample receiving container.
9. The apparatus of claim 8 wherein said needles connect to said sample port and also to a purge gas discharge outlet through a filter means.
10. The apparatus of claim 9 wherein said filter means comprises an absorbent for the process fluid vapors.

* * * * *